US012577519B2

(12) United States Patent
Heinrichs

(10) Patent No.: US 12,577,519 B2
(45) Date of Patent: Mar. 17, 2026

(54) BIOREACTOR CLEANING SYSTEM WITH AN ACID TANK AND A DEVICE FOR NEUTRALIZING THE ACID

(71) Applicant: VOGELSANG GMBH & CO. KG, Essen (DE)

(72) Inventor: Martin Heinrichs, Essen (DE)

(73) Assignee: VOGELSANG GMBH & CO. KG, Essen (DE)

( * ) Notice: Subject to any disclaimer, the term of this patent is extended or adjusted under 35 U.S.C. 154(b) by 653 days.

(21) Appl. No.: 18/015,743

(22) PCT Filed: Jul. 13, 2021

(86) PCT No.: PCT/EP2021/069425
§ 371 (c)(1),
(2) Date: Jan. 12, 2023

(87) PCT Pub. No.: WO2022/013201
PCT Pub. Date: Jan. 20, 2022

(65) Prior Publication Data
US 2023/0220324 A1     Jul. 13, 2023

(30) Foreign Application Priority Data
Jul. 13, 2020    (DE) ..................... 20 2020 104 033.2

(51) Int. Cl.
*C12M 1/00*      (2006.01)
*C12M 1/06*      (2006.01)
*C12M 1/34*      (2006.01)
*C12M 1/36*      (2006.01)

(52) U.S. Cl.
CPC ............ *C12M 39/00* (2013.01); *C12M 27/02* (2013.01); *C12M 41/26* (2013.01); *C12M 41/44* (2013.01); *C12M 41/48* (2013.01)

(58) Field of Classification Search
None
See application file for complete search history.

(56) References Cited

U.S. PATENT DOCUMENTS

| | | | | |
|---|---|---|---|---|
| 8,153,006 | B1 * | 4/2012 | Fessler ................. | C02F 3/2853 |
| | | | | 210/603 |
| 2007/0128087 | A1 * | 6/2007 | Cannizzaro ............ | C12M 33/04 |
| | | | | 422/50 |
| 2014/0338707 | A1 * | 11/2014 | Cueni ....................... | B08B 9/08 |
| | | | | 134/95.2 |

FOREIGN PATENT DOCUMENTS

| | | |
|---|---|---|
| CN | 110790452 | 2/2020 |
| DE | 140488 | 3/1980 |
| DE | 19524960 | 1/1997 |
| DE | 102015222989 | 5/2017 |

(Continued)

*Primary Examiner* — Holly Kipouros
(74) *Attorney, Agent, or Firm* — PRICE HENEVELD LLP

(57) ABSTRACT

A bioreactor cleaning system for cleaning a bioreactor in a rail vehicle. A suction unit, a supply unit, an electronic control unit for actuating the suction unit and the supply unit, an acid tank, a collection tank for receiving a liquid suctioned out of the bioreactor, and a freshwater connection are provided. The bioreactor cleaning system comprises a metering unit which has acid canister connections, base canister connections, an acid metering device which can be connected to the acid canister connections and the acid tank, and a base metering device which can be connected to the base canister connections and the acid tank. Additionally, a mixer is provided in order to mix the different liquids.

26 Claims, 7 Drawing Sheets

(56)     References Cited

FOREIGN PATENT DOCUMENTS

| DE | 102016115393 | 12/2017 |
| DE | 202017101065 | 5/2018 |
| DE | 102017208852 | 11/2018 |
| EP | 1559775 | 8/2005 |
| EP | 2098280 | 9/2009 |
| EP | 2364893 | 9/2011 |
| EP | 2789683 | 10/2014 |
| EP | 3404090 | 11/2018 |
| WO | 03010097 | 2/2003 |
| WO | 2017207494 | 12/2017 |

* cited by examiner

BIOREACTOR CLEANING SYSTEM WITH AN ACID TANK AND A DEVICE FOR NEUTRALIZING THE ACID

CROSS-REFERENCE TO FOREIGN PRIORITY APPLICATION

The present application claims the benefit under 35 U.S.C. §§ 119(b), 119(e), 120, and/or 365(c) of PCT/EP2021/069425 filed Jul. 13, 2021, which claims priority to German Application No. DE 20 2020 104 033.2 filed Jul. 13, 2020.

FIELD OF THE INVENTION

The invention relates to a bioreactor cleaning system for cleaning a bioreactor, preferably a bioreactor in a rail vehicle, with a suction unit for suctioning liquid from the bioreactor, the suction unit having a suction connection for connecting to the bioreactor, a supply unit for feeding liquid into the bioreactor, the supply unit having at least a first supply connection for connecting to the bioreactor, an electronic control unit for controlling the suction unit and the supply unit, an acid tank for receiving an aqueous acid solution, and a collection tank for receiving liquid suctioned from the bioreactor, and a freshwater port for supplying freshwater to the bioreactor cleaning system, wherein the supply unit is connected to the freshwater port and the acid tank to selectively provide freshwater and/or aqueous acid solution to the first supply connection, and wherein the suction unit for suctioning liquid from the bioreactor is selectively connectable to the acid tank or collection tank for supplying acid solution suctioned from the bioreactor to the acid tank and substantially pH-neutral residual fluid suctioned from the bioreactor to the collection tank. In stationary systems, the collection tank may also be omitted and the fluid suctioned or extracted from the bioreactor may be fed directly to a drain. The invention also relates to a method for operating a bioreactor cleaning system, and a computer program.

BACKGROUND OF THE INVENTION

Conventional bioreactors have a solids tank with a filter basket into which wastewater with solid and liquid components is fed. The filter basket separates the solid from the liquid components. For this purpose, the filter basket has filter elements on the surrounding walls, such as the bottom and side walls, through which liquid elements can flow and by means of which solid elements are collected. The solid elements collect at the bottom inside the filter basket separated from the liquid elements and form a filter cake. The liquid elements flow through the filter elements into the solids tank and from there into a liquid tank which is in fluid communication with the solids tank.

It is known that the solid elements in the filter basket settle as a filter cake. First, a filter cake is formed starting at a bottom side of the filter basket and then at the sides of the filter basket. As a result, the water is inhibited by the filter cake from flowing into the solids tank. A filter cake with some permeability results in an efficient filtration process. However, an increasingly thick and impermeable filter cake can cause the filter basket to clog. This results in an inefficient filtering process, as the liquid hardly passes through the filter anymore. It is, therefore, necessary to clean the filter basket of solids at regular intervals to ensure adequate drainage of the water into the solids tank.

It is known to remove the filter cake to counteract this clogging. Often, the filter cake is removed as soon as the first effects of clogging appear. However, this has the disadvantage that inefficient filtration has already taken place. It is also known to check the amount of filter cake from time to time to determine if removal is necessary. However, this has the disadvantage that the check is carried out randomly, and the correct time, i.e., neither too early nor too late, for removal of the filter cake cannot be reliably determined in this way. In addition, it is not possible to reliably assess whether the filter cake is already so impermeable that it must be removed.

One problem with such cleaning processes, however, is that bioreactor systems are usually constructed as closed systems and it is therefore very difficult to determine the degree of contamination and the cause of insufficient filtration. Existing bioreactors in particular often do not have interfaces that can be used to read out the information required to determine the cause of an error or the degree of contamination, or even data that is helpful for this purpose. This is particularly difficult if such a bioreactor is installed onboard a vehicle, such as a rail vehicle, in order to clean the wastewater that accumulates there. In such applications, it is often desired that maintenance and assurance of the bioreactor's function is decentrally possible and without the removal of the bioreactor from the vehicle. However, this desire usually cannot be satisfied due to the necessary compactness. Access to the bioreactor and to data describing its condition is not possible or only possible with great difficulty.

Furthermore, there is a problem in recycling or disposing of or neutralizing the acid used during cleaning. Usually, acid is added to the bioreactor to remove lime deposits or the like. This should be done not only in the bioreactor itself, but also in the pipes. However, the acid cannot be easily disposed of afterwards, but must be neutralized beforehand. On the one hand, this is time-consuming, and on the other hand there is a problem in setting the pH value correctly so that the acid neutralized in this way can then be disposed of.

It is an object of the invention to provide a bioreactor cleaning system, a method and a computer program of the type mentioned above, which allow a more efficient use of the acid.

SUMMARY OF THE INVENTION

This object is solved in a bioreactor cleaning system of the type mentioned above in that it has a metering unit which has one or more acid canister connections for connecting acid canisters and one or more base canister connections for connecting base canisters, an acid metering unit which can be connected on the input side to the one or more acid canister connections and on the output side to the acid tank and/or the bioreactor, and a base metering unit which can be connected on the input side to the one or more base canister connections and on the output side to the acid tank and/or the bioreactor, which can be connected on the input side to the one or more base canister connections and on the output side to the acid tank and/or the bioreactor, and a mixer, wherein the mixer can be connected on the input side to a fresh water connection and to the acid doser and/or base doser and on the output side to the acid tank and/or the bioreactor in order to supply the latter with a solution which can be used to neutralize the acid solution present in the acid tank and/or bioreactor.

The invention is based on the realization that by using the mixer, which is connected to the acid dosing unit and/or base dosing unit, a liquid can be provided which, on the one hand, can be used directly in the acid tank as an aqueous acid solution, but, on the other hand, enables both a subsequent dosing of acid and neutralization by the selective addition of base. This means that it is no longer necessary to collect the acid in the acid tank in a first step, which has been suctioned from the bioreactor after a cleaning process, for example, and then in a second step transport it to a station where the acid solution suctioned from the bioreactor is then neutralized by adding base. Rather, the used acid is neutralized directly in the bioreactor cleaning system and can then be disposed of. However, the dosing unit can also be connected directly to the bioreactor via appropriate lines and valves, for example, via the supply unit. In this way, acidic liquid that can be used for cleaning can be fed directly from the metering unit into the bioreactor. In addition, it is possible, after completion of the cleaning process, to neutralize the aqueous acid solution present in the bioreactor by appropriate addition of base by means of the metering unit in the bioreactor itself. This can save freshwater that would otherwise have to be used for rinsing the bioreactor after cleaning the bioreactor with aqueous acid solution.

Preferably, the bioreactor purification system comprises a first pH sensor for sensing a first pH value of a fluid supplied to the acid tank and for providing a first pH signal to the electronic control unit. The first pH sensor is preferably located downstream of the mixer and upstream of an inlet of the acid tank. In this way, the first pH sensor can sense the pH of the fluid in the acid tank. Inlets other than the inlet from the first pH sensor into the acid tank are preferably not provided.

Furthermore, it is preferred that a second pH sensor is provided for detecting a second pH value of a liquid suctioned via the suction connection. The second pH sensor can also be additionally or alternatively arranged upstream of the mixer. Preferably, fluid that has been suctioned from the bioreactor via the suction port is passed through the bioreactor cleaning system such that the second pH sensor and/or the first pH sensor can detect the pH of that fluid. Preferably, the fluid is guided from the suction port within the bioreactor cleaning system such that it is first delivered to the second pH sensor, then to the mixer, then to the first pH sensor, and then into the acid tank. The bioreactor cleaning system preferably has corresponding piping and valves inside, and the valves can be partially or fully controlled by the electronic control unit.

In a preferred further embodiment, the acid doser has an acid ejector that is connectable to the fresh water port on the input side. The acid ejector thus has two input ports, namely one that is connectable or connected to the one or more acid canister ports and one that is connectable or connected to the fresh water port. Acid from the one or more acid canisters and fresh water are then mixed in the acid ejector and then provided to the mixer.

In a corresponding manner, the base metering device preferably has a base ejector that is connectable to the fresh water connection on the input side. Thus, the base ejector also has two inputs, namely one that is connected or connectable to the one or more base canister ports and one that is connected or connectable to the freshwater port. Base and freshwater are then mixed in the base ejector and fed to the mixer. In this way, a particularly simple metering of acid and base can be achieved. Preferably, valves are connected upstream and downstream of the acid and base ejectors, respectively, in order to be able to control the mixing of acid and base into freshwater even better. Preferably, these upstream and downstream valves are in turn connected to the electronic control unit so that they can be controlled by the electronic control unit. Preferably, the mixer also has a freshwater throttle for throttling the freshwater supplied to the mixer. This further enables the dosing of acid, base, and freshwater to be controlled even better. The throttle is also preferably connected to the electronic control unit so that it can be controlled and adjusted by the electronic control unit.

In another preferred embodiment, the bioreactor cleaning system comprises a first flow meter for measuring freshwater supplied to the mixer and/or the acid doser and/or the base doser. The first flow meter may be located upstream of the mixer and downstream of a freshwater connection. In order to provide a proper dosage of acid, base, and freshwater to the acid tank, it is advantageous to know the flow rate of the freshwater. The flow meter preferably provides a flow rate signal to the electronic control unit so that the electronic control unit can control the dosing of acid and base as a function thereof and as a function of a desired pH value.

Preferably, a second flow meter is provided for measuring the acid supplied to the acid doser. Again, it is advantageous to know the flow rate. This is particularly relevant if, for example, the acid tank is to be initially filled with an aqueous acid solution at the start or before cleaning, and in this respect only acid and freshwater are mixed. Although it is also possible to measure the pH value in the acid tank, the flow meter can detect a flow rate present prior to mixing, so that a mixture can be generated based on the volume flows of acid and freshwater.

In a further preferred embodiment, the suction unit and/or the supply unit are operable to pump liquid out of the acid tank to the mixer and back into the acid tank. In this way, additional acid and/or base can be added to the liquid present in the acid tank. If acid or base were added directly to the acid tank, it would have to be mixed there. Since this is not readily possible, there is usually a concentration gradient in the acid tank in the prior art. By pumping cyclically from the acid tank to the mixer and back to the acid tank, it is possible to achieve a very homogeneous liquid in the acid tank, which advantageously can be used for cleaning the bioreactor. It is also easier to neutralize the acid present in the acid tank in this way. In the prior art, on the other hand, there is the problem that although sufficient base is added to the acid in the acid tank, due to the concentration gradient, limit values are then exceeded at points and/or in sections during disposal, as a result of which pipes can be damaged and environmental regulations cannot be complied with. By supplying the liquid present in the acid tank to the mixer and from there back to the acid tank, this problem is eliminated and a homogeneous liquid can be achieved.

Alternatively or additionally, the suction unit and/or the supply unit are operable to pump liquid out of the bioreactor to the mixer and back into the bioreactor. This allows the aqueous acid solution to be neutralized in the bioreactor itself after the bioreactor has been cleaned. For this purpose, the liquid is suctioned out of the bioreactor, preferably by means of the suction unit, then conveyed to the dosing unit, in which base is added, and then back into the bioreactor, preferably by means of the supply unit. This cycle can be repeated until a desired neutral pH is reached. If too much base has been added in the meantime, acid may have to be added in order to slightly acidify again.

Additionally or alternatively, the suction unit and/or the supply unit are preferably operable to pump liquid out of the acid tank and/or the bioreactor to the first or second pH sensor and back to the acid tank and/or bioreactor. In this way, the pH of the fluid in the acid tank and/or bioreactor can be easily determined. If the second pH sensor is located upstream of the mixer, the liquid is first directed to the second pH sensor, then to the mixer, then to the first pH sensor, and back to the acid tank. That is, at the second pH sensor, the pH of the liquid drawn from the acid tank can first be determined, and then acid or base can be added to the mixer as needed. At the first pH sensor, this mixture can then be controlled, fed back to the acid tank, and so on until a corresponding pH value is detected at the second pH sensor, i.e., at the input of the mixer. Preferably, at the input and output of the mixer, the pH value is the same when the target pH value has been reached.

In a further preferred embodiment, the electronic control unit is adapted to determine an acid quality value indicative of a quality of aqueous acid solution present in the acid tank, compare the determined acid quality value with a predetermined acid comparison value, and in dependence on the comparison: Initiating neutralization of the aqueous acid solution in the acid tank. Such acid quality value may be, for example, a loading of solids, a degree of contamination, or the like.

Particularly preferred, the acid quality value is the first pH value and the electronic control unit is adapted to determine the first pH value of aqueous acid solution present in the acid tank, compare the determined first pH value with a predetermined pH threshold value and, in the event that the determined first pH value exceeds the pH threshold value: Initiating neutralization of the aqueous acid solution in the acid tank. Preferably, the aqueous acid solution present in the acid tank is used for at least one cleaning cycle of a bioreactor. In a cleaning cycle, the aqueous acid solution is supplied to the bioreactor via the supply connection, is passed within the bioreactor through various conduits and/or screens or the like, and then the acid thus utilized and thereby partially or completely consumed is suctioned via the suction port into the bioreactor cleaning system, where it is again supplied to the acid tank. It has been shown that two or more cleaning processes can also be carried out with this aqueous acid solution, but not as many as desired. After a certain number of cleaning operations, depending on the degree of contamination of the bioreactor, the acid solution is finally used up. This is preferably determined by the acid quality value, or preferably the first pH value, exceeding the pH threshold.

The electronic control unit is preferably designed to determine and load the acid comparison value and/or the predetermined pH threshold value from a database. The acid comparison value and/or the predetermined pH threshold value can be dependent on the type of bioreactor, the type of acid used, or other parameters. Depending on these parameters, the electronic control unit then determines the corresponding values and loads them from a database, or from a remotely located memory, for example, via the Internet, or from a cloud service.

In another preferred embodiment, for neutralizing the aqueous acid solution present in the acid tank, the electronic control unit is adapted, while the suction unit and/or the supply unit is pumping the liquid out of the acid tank to the first or second pH sensor and back into the acid tank, to cause the base doser to dispense base into the mixer until a neutral target pH in the acid tank is reached. In this way, a continuous neutralization can be achieved in which only as much base as required is used. In addition, a homogeneous liquid is always achieved, so that neither too much nor too little base is added and thus efficient neutralization of the base is achieved.

In a second aspect, the invention solves the above-mentioned problem by a method for operating a bioreactor cleaning system, preferably a bioreactor cleaning system according to one of the preferred embodiments of a bioreactor cleaning system according to the first aspect of the invention described above, the method comprising the steps of: Determining an acid quality value indicative of a quality of aqueous acid solution present in an acid tank of the bioreactor cleaning system, comparing the determined acid quality value with a predetermined acid comparison value, and depending on the comparing: Initiating neutralization of the aqueous acid solution in the acid tank.

The process is based on the idea that, depending on the quality of the acid solution in the acid tank, a neutralization process should be carried out. The aqueous acid solution present in the acid tank is used at least once to clean the bioreactor. With each time the aqueous acid solution in the acid tank is used by supplying it to the bioreactor, then extracting it from the bioreactor and returning it to the acid tank, the quality of the aqueous acid solution may deteriorate. Accordingly, in accordance with the method, a comparison of an acid quality value with a predetermined acid comparison value is preferably performed. Depending on this comparison, in particular, if the acid quality value falls below the predetermined acid comparison value, a neutralization of the aqueous acid solution is initiated. This is necessary in order to be able to dispose of the aqueous acid solution after neutralization. The neutralization is preferably a continuous neutralization.

Particularly preferred, the acid quality value is a first pH value. The pH value of the aqueous acid solution is particularly suitable as an acid quality value, since it can be used to make a statement about the ability of the aqueous acid solution to dissolve calcifications in the bioreactor. In this case, the method then preferably comprises the steps of: determining the first pH value of aqueous acid solution present in the acid tank, and comparing the determined first pH value with a predetermined pH threshold value, which is then the acid comparison value in this case. If the determined first pH value exceeds the pH threshold value, i.e., the aqueous acid solution is no longer acidic enough, neutralization of the aqueous acid solution is initiated.

It is further preferred that the method comprises: Determining and loading the acid comparison value and/or the predetermined pH threshold value from a database. The database may be provided internally within the bioreactor purification system or transmitted via a remote system, such as the Internet or a cloud service. The acid comparison value and/or the predetermined pH threshold value may be dependent on parameters entered into the device by a user or on values detected via the aqueous acid solution by means of one or more sensors.

Preferably, the method further comprises the steps of: pumping liquid out of the acid tank to a mixer of the bioreactor purification system and back into the acid tank. Preferably, the method further comprises, while pumping liquid out of the acid tank to a mixer of the bioreactor cleaning system and back into the acid tank: neutralizing the liquid. Preferably, the method further comprises: mixing in the mixer acid and/or base and/or fresh water. By mixing in acid, base, or freshwater, the liquid can be neutralized or its pH can be further adjusted. This is preferably done in the mixer and not in the acid tank directly. In this way, continuous neutralization or continuous acidification is possible in order to be able to adjust the pH value of the aqueous acid solution in the acid tank precisely.

Preferably, a first pH value is further detected downstream of the mixer. Preferably, a second pH value is sensed upstream of the mixer. By sensing the first and second pH values, it is possible to control the mixing of acid, base, or freshwater into the liquid stream in the mixer. For this reason, the method preferably further comprises the step: Depending on the first and/or second pH values, mixing acid and/or base into the mixer to achieve a target neutral pH value in the acid tank. The neutral target pH value is preferably in a range of 6.5 to 10. A range of 6.5 to 9, 7 to 9, or, in particular, 7 to 8 is also preferred. Instead of the neutral target pH value, any other pH value can also be adjusted. Basically, it is sufficient to detect one pH value, namely the first or second pH value, to form a closed control loop in this way. However, sensing two pH values, upstream and downstream of the mixer, allows for more accurate control and also allows fluid to be routed past the mixer, directly to the first pH sensor, for example, when mixing in acid, base, or freshwater is not desired. For example, it may be conceivable and preferred to supply fluid drawn from the bioreactor only to the first pH sensor, without using a pass through the mixer and the second pH sensor.

The method preferably further comprises the step: When the neutral target pH is reached: pumping the liquid from the acid tank to a collection tank of the bioreactor cleaning system and/or a disposal channel. The bioreactor cleaning system collection tank can be used to collect other liquids, such as residual liquid extracted from the bioreactor or liquid used in a mechanical cleaning process. The liquid in the collection tank can then be disposed of. The acid tank is usually designed to be much smaller than the collection tank, so it is preferred to bring the neutralized liquid from the acid tank into the collection tank. The acid tank is then empty and a new aqueous acid solution can be mixed, for example, to carry out another cleaning process of a bioreactor without having to empty the collection tank first. If the bioreactor cleaning system is not designed as a mobile system but as a stationary system, it is not necessary to temporarily store the neutralized liquid in the collection tank; in this case it can be fed directly into a disposal channel.

The method may further provide that, in response to comparing the determined acid quality value to the predetermined acid comparison value, the steps: Supplying liquid from the acid tank to the bioreactor for cleaning the bioreactor, suctioning liquid from the bioreactor, and supplying the suctioned liquid to the acid tank. These steps are preferably performed when the determined acid quality value exceeds the acid comparison value or it is determined that the quality of the aqueous acid solution in the acid tank is sufficient.

To improve the cleaning efficiency of the aqueous acid solution, the method may further comprise the step: Introducing air bubbles into the liquid while supplying the liquid to the bioreactor. In this way, oxygen is added to the aqueous acid solution supplied to the bioreactor as a liquid, whereby a chemical reaction between the aqueous acid solution and lime in the bioreactor may be enhanced. In addition, air can also be introduced when circulating liquid and/or aqueous acid solution through lines of the bioreactor cleaning system and/or the bioreactor. Hereby, mechanical cleaning of the lines can additionally be achieved by the air bubbles.

In a third aspect, the invention solves the above problem by a computer program product comprising code means which, when executed on a computer, causes a bioreactor cleaning system to perform the steps of the method according to one of the above preferred embodiments of a method according to the second aspect of the invention. The computer is preferably part of the bioreactor cleaning system. The computer program product is preferably provided on a storage means, such as, in particular, an optical storage means, or as a download.

Embodiments of the invention are now described below with reference to the drawings. These are not necessarily intended to show the embodiments to scale; rather, where useful for explanation, the drawings are in schematized and/or slightly distorted form. With regard to additions to the gauges directly recognizable from the drawings, reference is made to the relevant prior art. It should be borne in mind that a wide variety of modifications and changes concerning the shape and detail of an embodiment can be made without departing from the general idea of the invention. The features of the invention disclosed in the description, in the drawings as well as in the claims may be essential for the further development of the invention both individually and in any combination. In addition, all combinations of at least two of the features disclosed in the description, the drawings and/or the claims fall within the scope of the invention. The general idea of the invention is not limited to the exact form or detail of the preferred embodiments shown and described below, or limited to any subject matter that would be limited as compared to the subject matter claimed in the claims. In the case of stated design ranges, values lying within the stated limits are also intended to be disclosed as limiting values and to be capable of being used and claimed as desired. For simplicity, identical reference signs are used below for identical or similar parts or parts with identical or similar function.

BRIEF DESCRIPTION OF THE DRAWINGS

Further advantages, features, and details of the invention will be apparent from the following description of preferred embodiments and from the drawings. The drawings show in.

DETAILED DESCRIPTION OF THE EMBODIMENTS

Figure 1:
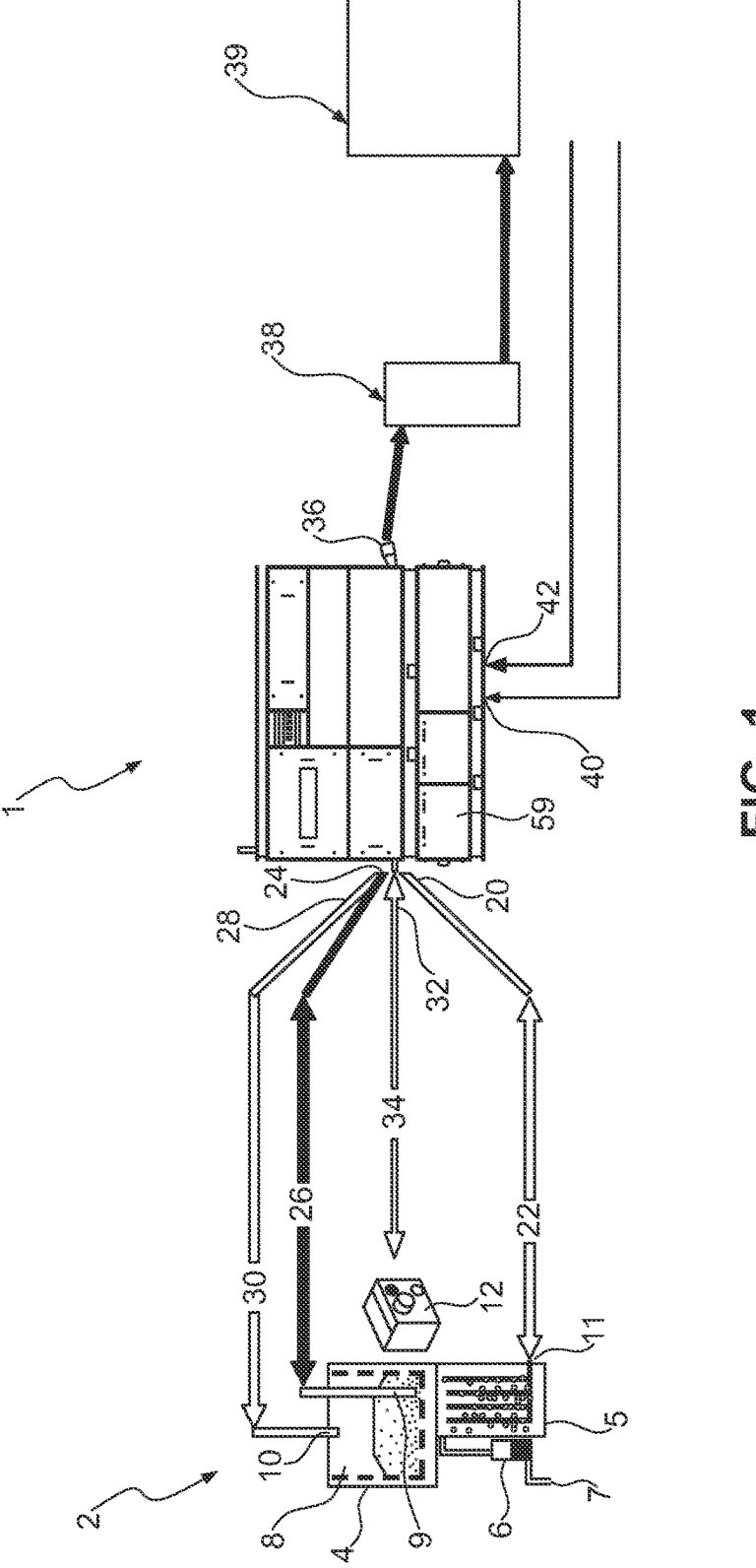
FIG. 1 is a schematic representation of the bioreactor cleaning system in connection with a bioreactor as well as further elements.

A bioreactor cleaning system 1 can be designed as a mobile bioreactor cleaning system, as shown in FIG. 1, or as a stationary bioreactor cleaning system. A mobile bioreactor cleaning system can typically be moved to a train in which a bioreactor 2 is provided. Bioreactors 2 in trains are generally known and will not be further described in detail here. In FIG. 1, a vertically oriented bioreactor 2 is shown as an example, with a solids tank 4, a liquid tank 5, and a sanitizer 6, which has an outlet 7, for draining liquid. A filter basket 8 is provided in the solids tank 4, into which both a 2-inch hose 9 terminates near the bottom and a cleaning nozzle 10 is provided to supply water under high pressure to the solids tank 4 to clean off a filter cake built up in the filter basket 8. A 1-inch connection 11 is further provided on the liquid tank 5 to draw or suction liquid from or supply liquid to the liquid tank 5. Further, the bioreactor 2 comprises a controller 12 that can, for example, read sensors of the bioreactor 2.

The bioreactor cleaning system 1 has connections via which it can be connected to the bioreactor 2. For example, in order to suction liquid from the bioreactor 2, the bioreactor cleaning system 1 has a suction connection 20, which can be connected to the 1-inch connection 11 of the liquid tank 5 of the bioreactor 2 via a suction line 22. Furthermore, the bioreactor cleaning system 1 has a supply connection 24, which can be connected to the 2-inch hose 9 of the bioreactor 2 via a feed line 26, in order to feed liquid into the bioreactor 2, more specifically the solids tank 4, via the latter. The bioreactor cleaning system 1 also has a high-pressure connection 28, which can be connected to the cleaning nozzle 10 via a high-pressure hose 30, and an electronic control connection 32, which can be connected to the control 12 of the bioreactor 2 via a signal line 34.

The bioreactor cleaning system 1 further has a disposal connection 36, via which the bioreactor cleaning system 1 can be connected to an external tank 38, which is connected to an external vacuum source 39, for extracting liquid from the bioreactor cleaning system 1. On the input side, the bioreactor cleaning system 1 has a power connection 40 and a fresh water connection 42.

Figure 2:
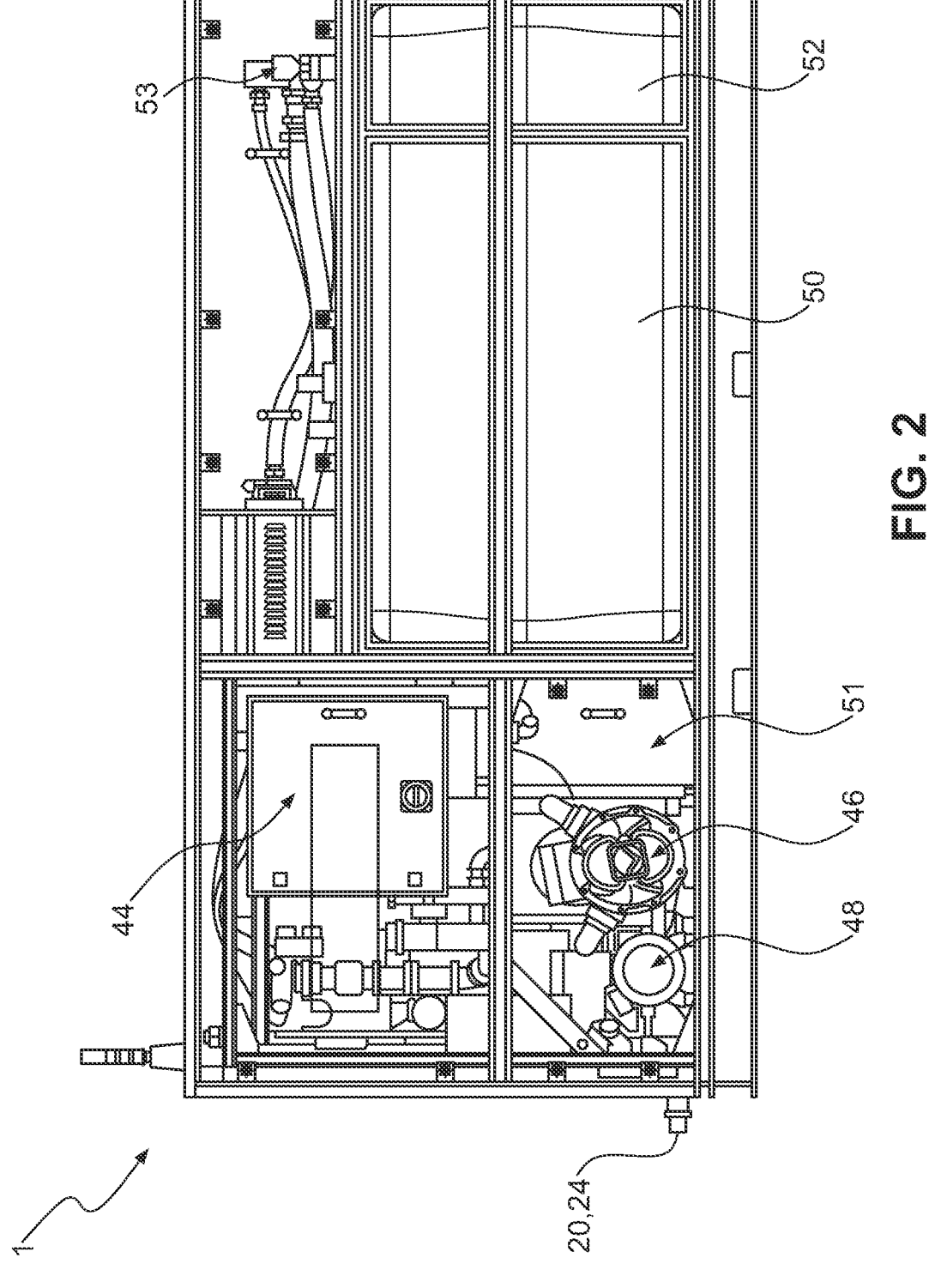
FIG. 2 is a schematic side view of the bioreactor cleaning system, partially cut free.

Inside the bioreactor cleaning system 1 (FIG. 2), the latter has an electronic control unit 44 which has a memory with program code and a processor for executing the program code. The electronic control unit 44 controls various functions of the bioreactor cleaning system 1, as is apparent, in particular, from the further description. For example, the electronic control unit 44 controls a pump 46 as well as a high pressure pump 48. The pump 46 can be used to provide a vacuum at the suction port 20 as well as to pump fluid to the supply connection 24. The high pressure pump 48 is used to provide a fluid at high pressure to the high pressure port 28. Furthermore, a collection tank 50 and an acid tank 52 are provided inside the bioreactor cleaning system 1, wherein a first level sensor 51 is provided for the collection tank 50 and a second level sensor 53 is provided for the acid tank 52.

Figures 3A, 3B, 3C, 3D:
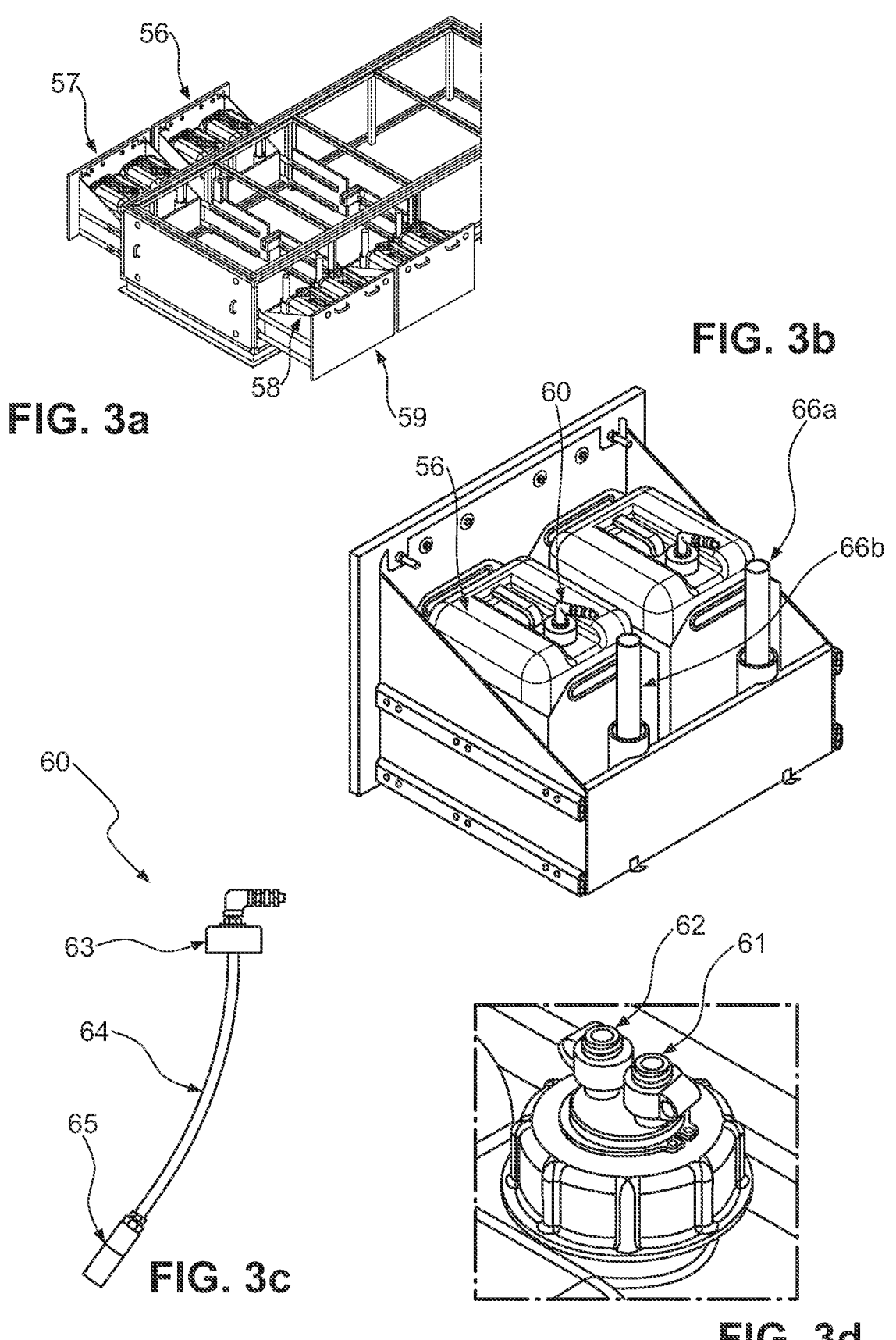
FIGS. 3a-3d are four representations of acid canisters.

A plurality of acid canisters 56 and a plurality of base canisters 58 are provided in a lower portion of the bioreactor cleaning system 1. The acid canisters 56 and base canisters 58 are respectively housed in acid drawers 57 and base drawers 59 provided for the purpose. FIG. 3*b* shows two acid canisters 56 in detail. A suction lance 60 is arranged at the acid canister 56, which can be connected to the acid tank 52 via further valves, as will be described with reference to FIG. 4. Adjacent to the suction lance 60, which is inserted into a suction port 61, an aeration valve 62 is provided. The suction lance 60 has a screw cap 63 (cf. FIG. 3*c*), a lance body 64, and a foot valve 65 with a fixed filter. If one of the canisters 56, 58 has to be changed, the suction lance 60 can be inserted in lance holders 66*a*, 66*b* provided for this purpose on the respective drawers so that it is not damaged.

Figure 4:
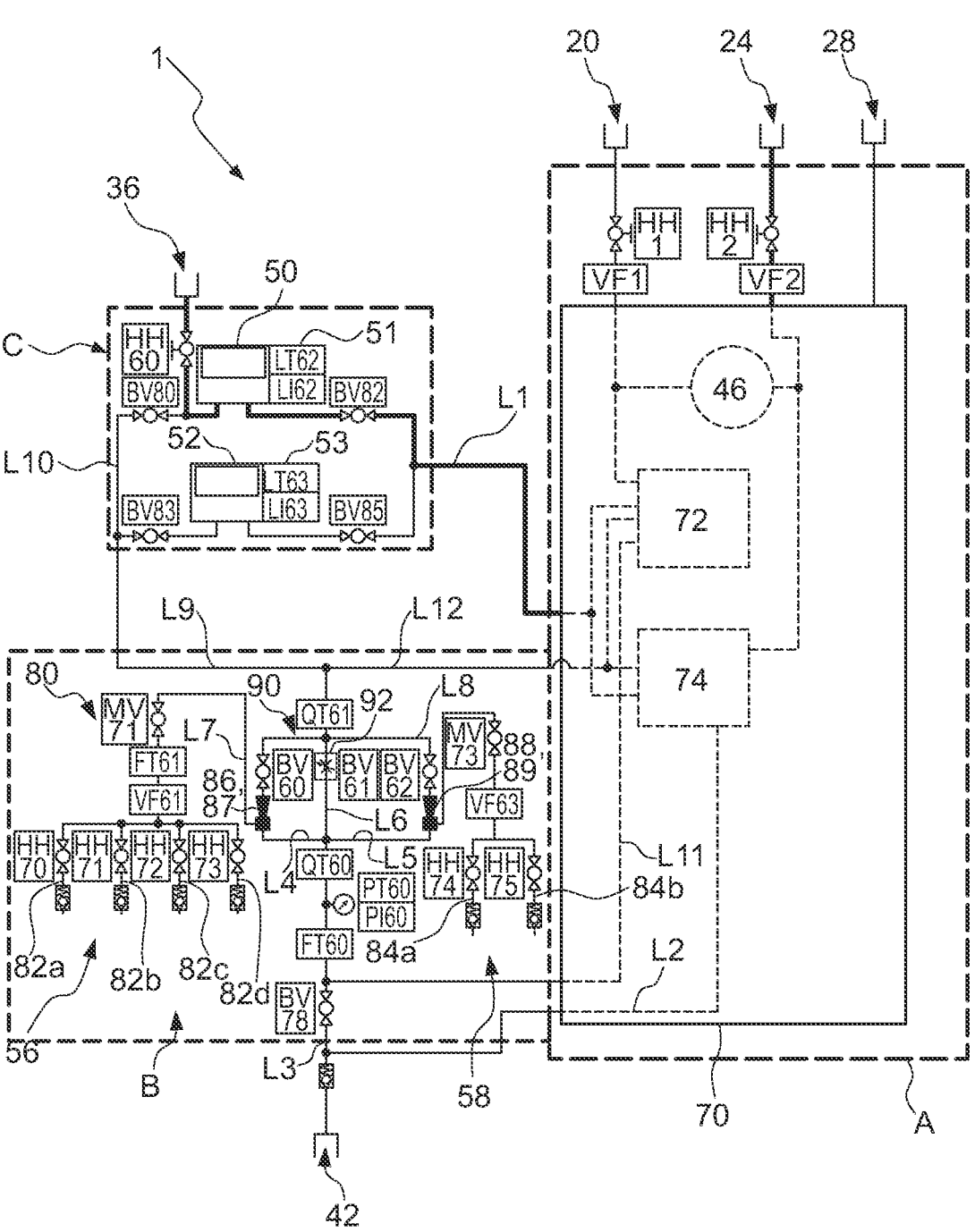
FIG. 4 is a circuit diagram of the bioreactor cleaning system.

FIG. 4 illustrates a circuit diagram or layout of the bioreactor cleaning system 1. Power connection 40 is not shown, nor is electronic control unit 44. The circuit diagram according to FIG. 4 is divided into three systems, with system boundaries A, B, and C. System boundary A in the right-hand side of FIG. 4 comprises, in addition to suction connection 20, supply connection 24 and high-pressure connection 26, a pump and valve unit 70, which is shown here only schematically as a block, but inside which a plurality of valves, conduits, sensors, and the like may be arranged. As part of the pump and valve unit 70, pump 46 is shown here, for example, as well as schematically a suction unit 72 and a supply unit 74 of the bioreactor cleaning system 1. Suction unit 72 serves to suction, extract, or draw liquid from bioreactor 2 and has suction connection 20 for this purpose. Pump 46 acts thereon to provide a vacuum at suction connection 20. Furthermore, supply unit 74 is formed in the pump and valve unit 70 and has supply connection 24.

Figure 5:
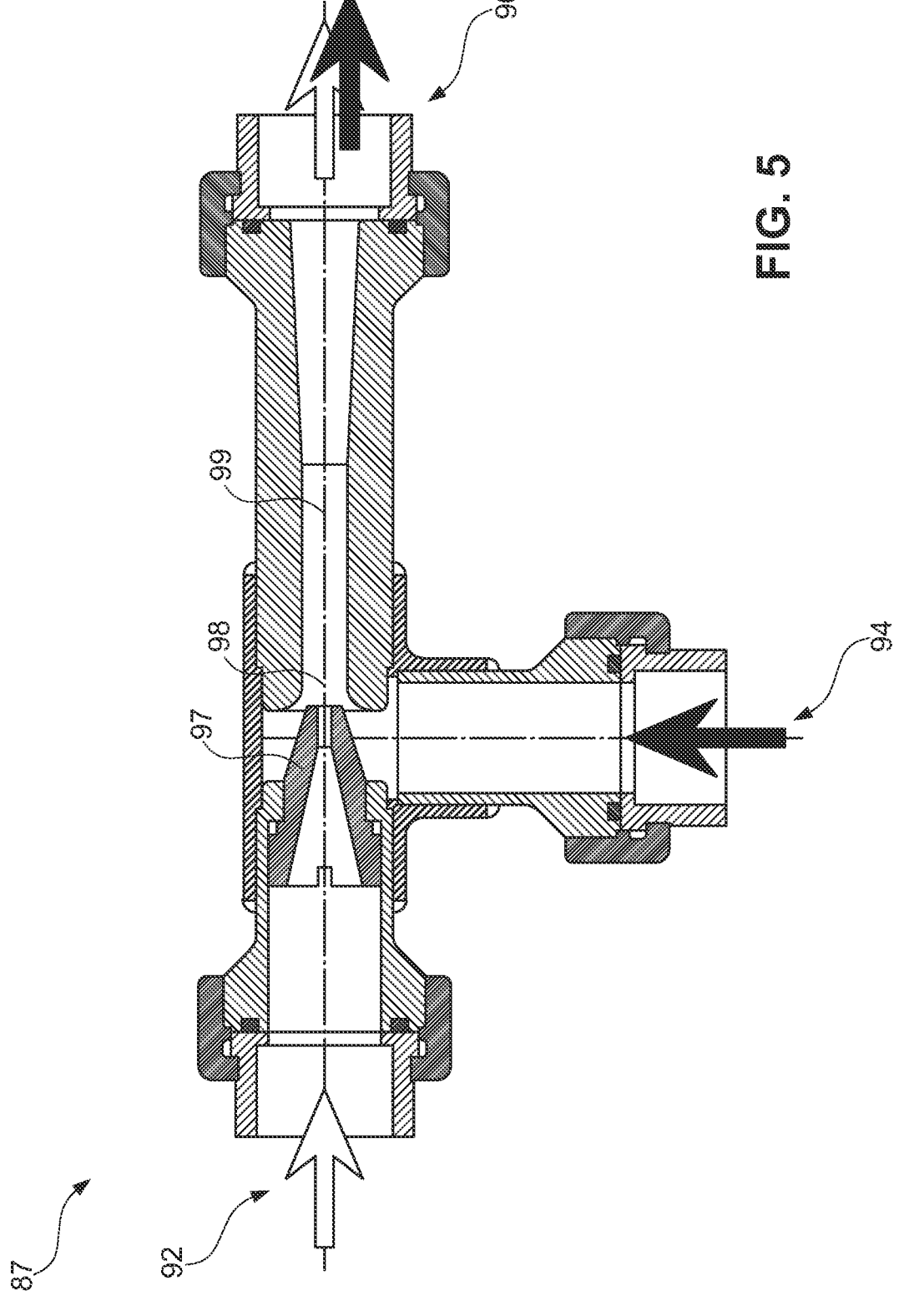
FIG. 5 is a cross section of an ejector.

A dosing unit 80 is within system boundary B, as are the plurality of acid canisters 56 and plurality of base canisters 58. Freshwater connection 42 is shown here within system B, more specifically associated with dosing unit 80. In the embodiment shown, dosing unit 80 has four acid canister connections 82*a*, 82*b*, 82*c*, 82*d* and two base canister connections 84*a*, 84*b*. Dosing unit 80 is then in turn connected to a structural unit within system boundary C, in which collection tank 50 and acid tank 52 are also shown in the embodiment present embodiment (FIG. 5). Likewise, first level sensor 51 and second level sensor 53 are shown within this system boundary, as is disposal connection 36. System boundaries A, B, and C are for illustrative purposes only, but have no structural influence beyond that. In certain embodiments, however, the system boundaries may form structural boundaries.

As part of a cleaning of bioreactor 2, residual fluid present in bioreactor 2, in particular, liquid tank 5, can now first be suctioned in the first step with suction unit 72 via suction connection 20 under the action of pump 46. This residual fluid is then supplied to collection tank 50 via a first line L1. For this purpose, a valve BV82, which is preferably designed as a ball valve, is opened, which is preferably initiated by electronic control unit 44. A first manual valve HA1 is arranged at suction connection 20, which is to be opened manually. Downstream of this in the direction of the pump and valve unit 70, a first flow measuring unit VF1 comprising a capacitive sensor is arranged. By means of the capacitive sensor of flow measuring unit VF1, the presence of liquid can be determined in order to close the line for the case that no liquid is present, or to provide no further vacuum, or to use it at another position. Flow measuring unit VF1 is also connected to electronic control unit 44 to provide appropriate flow signals thereto. If the residual fluid has now been extracted from the bioreactor 2, it may be useful and necessary to first either carry out mechanical cleaning using the nozzle head 10, or to introduce liquid via 2-inch hose 9 in order to detect the permeability of filter basket 8. For this purpose, freshwater can be supplied via supply connection 24, for example. In this embodiment, a second manual valve HA2 is to be opened manually for providing the freshwater supply. The supply unit 74 is connected to freshwater connection 42 via a second line L2 and receives freshwater from the latter. Supply unit 74 can then forward this liquid to supply connection 24 using the action of pump 46.

In the course of chemical cleaning, bioreactor 2 is cleaned by means of a chemical substance, namely, in particular, an aqueous acid solution. Here, it may be necessary to first prepare the aqueous acid solution. In the embodiment shown here, this is done by means of dosing unit 80. Dosing unit 80 is connected to freshwater connection 42 via a third line L3. A valve BV78, preferably a ball valve, is placed in third line L3, which can be controlled by means of electronic control unit 44. Downstream, a first flow sensor FT60, a pressure sensor PT60, and a second pH sensor QT60 are arranged. Downstream of second pH sensor QT60, the line branches into a fourth line L4 leading to an acid doser 86, a fifth line L5 leading to a base doser 88, and a sixth line L6 forming a bypass for freshwater to acid doser 86 and base doser 88. Acid dosing unit 86, which in this embodiment is designed as an acid ejector 87 (cf. FIG. 5), not only receives freshwater via fourth line L4, but is also connectable or connected to acid canister connections 82*a*-82*d* via a seventh line L7. More specifically, seventh line L7 is connected to acid canister ports 82*a*-82*d* via a first solenoid valve MV71, a second flow sensor FT61, and a third flow meter VF61. Flow meter VF61 is again equipped with a capacitive sensor and detects the presence of liquid. Thus, it can be used as a canister empty detection device. Flow sensor FT61, on the other hand, measures a volumetric flow and preferably uses an impeller. First solenoid valve MV71, second flow sensor FT61, and third flow meter VF61 are in turn connected to electronic control unit 44 to provide signals thereto or to be controlled thereby. Downstream of acid dosing unit 86, a valve BV60 is arranged, which in turn is preferably designed as a ball valve and can be controlled by electronic control unit 44.

In an analogous manner, base dosing unit 88 in this embodiment is designed as a base ejector 89 and is not only supplied with freshwater via fifth line L5, but also with base via an eighth line L8. For this purpose, eighth line L8 is connected to first and second base canister ports 84*a*, 84*b* via a valve MV73, preferably a ball valve, and a flow meter VF63. Flow meter VF63 may be identical in design to flow meter VF61. It can also be used as a canister empty detection device. Downstream of base metering device 88, a valve BV62 is arranged, which is preferably formed as a ball valve and is controllable by electronic control unit 44.

Acid ejector 87, base ejector 89, and sixth line L6 open together into a mixer 90. According to the embodiment shown here, an optional throttle 92 is arranged between sixth line L6 and mixer 90, which is adjustable via an actuator BV61. Actuator BV61 is also controllable by electronic control unit 44. In this way, by controlling valves BV60, BV62 or throttle 92 via actuator BV61, the flow rates of acidified fresh water via fourth line L4, freshwater via sixth line L6 and basified freshwater via fifth line L5 can be mixed together as required. Downstream of mixer 90, a first pH sensor QT61 is arranged to provide a first pH signal to electronic control unit 44. Mixer 90 is connected to acid tank 52 via a ninth line L9 and a further valve BV83, preferably designed as a ball valve. Thus, first pH sensor QT61 can be used to detect the pH of the fluid supplied to acid tank 52 via valve BV83. Alternatively, starting from mixer 90, the liquid can also be supplied to collection tank 50. For this purpose, a valve BV80 is provided, which connects a tenth line L10, which branches off from ninth line L9, to collection tank 50.

In this way, an aqueous acid solution can be generated in acid tank 52, which can then be used to clean bioreactor 2. To supply the aqueous acid solution from acid tank 52 to bioreactor 2, valve BV83 is closed and valve BV85, which is placed between acid tank 52 and first line L1, is opened. Subsequently, a vacuum can be built up in first line L1 using the pump 46 and the aqueous acid solution can be supplied to bioreactor 2 via valve BV85, first line L1, and supply unit 74 via supply connection 24.

The aqueous acid solution will then flow through bioreactor 2, more specifically through filter basket 8, and then into liquid tank 5. On this path, the acid of the aqueous acid solution reacts with adhering lime deposits and dissolves them. It is also possible to simultaneously introduce air in the form of bubbles during this process to increase the cleaning effect. This is particularly preferred for lines of bioreactor 2, which can and should also be cleaned.

Now that the liquid has passed through bioreactor 2, it can be drawn via 1-inch connection 11. This is done using suction unit 74 by means of pump 46.

The liquid thus drawn from bioreactor 2 can then be fed from the suction unit 72 either directly via the first line L1 and the valve BV85 in turn to the acid tank 52. However, it is also possible to feed the extracted liquid from the suction unit 72 via an eleventh line L11 into third line L3, in the embodiment shown here (FIG. 4) between valve BV78 and flow sensor FT60. If valves BV60, BV62 remain closed, the extracted liquid can be fed through second pH sensor QT60, throttle 92, and first pH sensor 61, then through ninth line L9, valve BV83, and into acid tank 52. In other embodiments, it may also be provided that line L11 opens into third, the sixth, or ninth line L3, L6, L9 at other locations. For example, eleventh line L11 could also open into sixth line L6 downstream of second pH sensor QT60, for example, between throttle 92 and first pH sensor 90. It could also be provided that a further pH is provided in first line L1 to directly measure the pH of the liquid extracted from bioreactor 2.

As long as the pH value of the extracted liquid passing first pH sensor QT61 falls below a predetermined pH threshold, the aqueous acid solution can be used again to clean bioreactor 2 or another bioreactor. The pH value of the extracted liquid is used here as the acid quality value. Other values can be used as well, such as, in particular, a loading of the liquid with dirt particles or the like.

If it is determined that the first pH value detected by first pH sensor QT61 exceeds a predetermined pH threshold, the aqueous acid solution in acid tank 52 should be neutralized for subsequent disposal. In order to perform neutralization, the extracted liquid is fed to dosing unit 80 either from suction connection 20 directly, or from acid tank 52 by means of suction unit 72 via eleventh line L11. Here, the aqueous acid solution to be neutralized is fed past flow sensor FT60, second pH sensor QT60, and then divided between fourth, fifth, and sixth lines L4, L5, L6. Here, base is added via the base dosing unit 88 so that the pH value of the aqueous acid solution to be neutralized is increased. The increased pH value can in turn be measured with first QT61 pH sensor. The liquid can then in turn be fed to acid tank 52 or via a twelfth line L12 back to suction unit 72 and from there back to eleventh line L11. The aqueous acid solution is thus neutralized as it circulates within bioreactor cleaning system 1, and in this manner flow neutralization is accomplished. Once a sufficiently high pH has been reached, the liquid is not returned to acid tank 82 via valve BV83, but is returned to collection tank 50 via valve BV80, from where it can be disposed of.

In addition to acid ejector 87 and base ejector 89, one or more other ejectors could also be provided, for example, to produce blue water mixtures for chemical toilets on trains using bioreactor cleaning system 1.

FIG. 5 illustrates an ejector which may be used as said acid ejector 87 and base ejector 89. By way of example, FIG. 5 illustrates acid ejector 87, but the same applies to base ejector 89. Acid ejector 87 has a first inlet 92 connected to fourth line L4 and receiving fresh water under pressure. It further has a second inlet 94 connected to seventh line L7 to receive acid. The ejector has an outlet 96 connected to valve BV60 (see FIG. 4). Inside the ejector a nozzle piece 97 is provided, which opens into an interspace 98 in the manner of a venturi pump, so as to draw acid from second inlet 94 and deliver it to a common ejector chamber 99. This common ejector chamber 99 leads to outlet 96 where freshwater and acid are mixed. To accurately dose the acid at second inlet 94, valve MV71 can be opened in a pulsed manner to adjust the pH of the mixed liquid at outlet 96 as accurately as possible.

Figure 6:
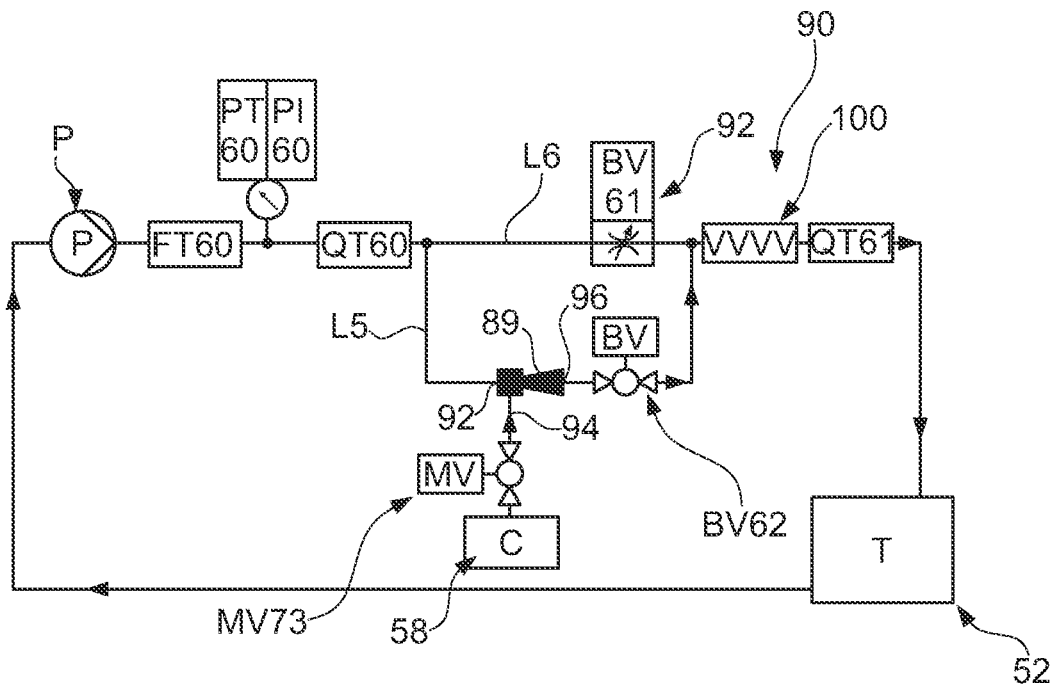
FIG. 6 is a schematic circuit diagram of a mixer with further elements.

FIG. 6 schematically illustrates the circuit of the flow-through neutralization. P indicates either the pump 46 or the freshwater connection 42 Important is that the circuit is set in motion. From there, the liquid then reaches first flow meter FT60, pressure sensor PT60 and second pH sensor QT60. The line branches on the one hand into line L6 and line L5, which leads to base ejector 89, more precisely to first inlet 92. Valve MV73 is connected to second inlet 94, via which base can be fed to second inlet 94 in the embodiment shown in FIG. 6. Dosing can then be further adjusted via valve BV62, while in sixth line L6 the other path can be regulated via throttle 92 and valve BV61.

In mixer 90, in which sixth line L6 and fifth line L5 as well as fourth line L4 (cf. FIG. 4) are combined, a diffuser 100 is also provided in the embodiment shown here. This is shown here only schematically and can be designed, for example, as a static mixer with various mixing elements. Downstream of diffuser 100, first pH sensor QT61 is provided. This circulation is carried out until a sufficiently high pH value has been reached in acid tank 52 to allow the aqueous solution to be disposed of.

Figure 7:
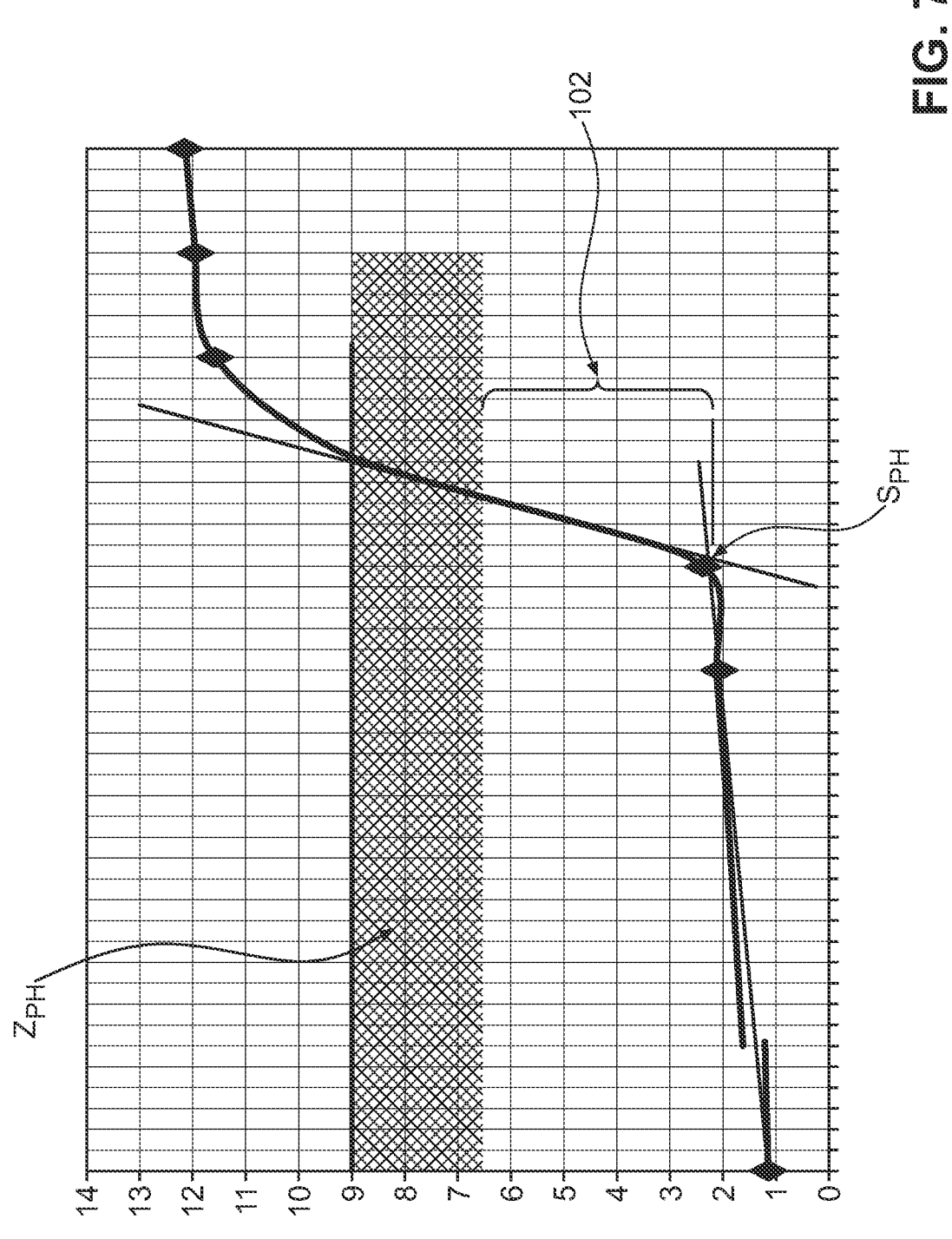
FIG. 7 is a diagram of the neutralization of the aqueous acid solution.

FIG. 7 now illustrates a characteristic curve of a neutralization of an aqueous acid solution. The pH value is plotted on the ordinate and the amount of base added on the abscissa. As can easily be seen from this graph, the pH value initially rises only slightly, even with a substantial amount added, in a first section up to about pH 2, then very sharply, up to a little pH 11/12, and then flattens out again. The neutral range between 6.5 and 9 is marked here with a background and the target pH value ZpH is also located here. The aqueous solution should be in this range in order to be disposed of. This graph illustrates why it is difficult to bring about neutralization in a stationary process within acid tank 52. In continuous neutralization, as proposed in the present invention, the neutral range between 6.5 and 9 pH can be gradually adjusted by the closed loop control system without provoking "overshoot." The diagram also shows the pH threshold SpH, which is used to measure whether or not the aqueous acid solution in acid tank 52 can continue to be used for purification. If it is determined that the aqueous solution in the acid tank 52 exceeds the pH threshold SpH, the neutralization process is initiated. In a range 102, the solution is no longer usable for cleaning, but it is also not yet neutral enough to be disposed of.

The invention claimed is:

1. A bioreactor cleaning system for cleaning a bioreactor, comprising:

a suction unit for suctioning liquid from the bioreactor, the suction unit having an suction connection for connecting to the bioreactor;

a supply unit for supplying liquid into the bioreactor, the supply unit having at least one supply connection for connecting to the bioreactor;

an electronic control unit for controlling the suction unit and the supply unit;

an acid tank for receiving an aqueous acid solution;

a collection tank for receiving liquid suctioned from the bioreactor;

a freshwater connection for supplying the bioreactor cleaning system with freshwater;

wherein the supply unit is connected to the freshwater connection and the acid tank to selectively provide freshwater and/or aqueous acid solution to the supply connection;

wherein the suction unit for suctioning liquid from the bioreactor is selectively connectable to the acid tank or the collection tank for supplying acid solution suctioned from the bioreactor to the acid tank and for supplying substantially pH-neutral residual fluid suctioned from the bioreactor to the collection tank;

a dosing unit, which has one or more acid canister ports for connecting acid canisters and one or more base canister ports for connecting base canisters;

an acid doser connectable on an input side to the one or more acid canister ports and on an output side to the acid tank, and a base doser connectable on an input side to the one or more base canister ports and on an output side to the acid tank; and a mixer, wherein the mixer can be connected on an input side to the freshwater connection and the acid doser and/or base doser, and on an output side to the acid tank in order to supply the acid tank with a solution usable to neutralize the acid solution present in the acid tank.

2. The bioreactor cleaning system of claim 1, including a first pH sensor for detecting a first pH value of a fluid supplied to the acid tank and for providing a first pH signal to the electronic control unit.

3. The bioreactor cleaning system according to claim 2, including a second pH sensor for detecting a second pH value of a liquid suctioned via the suction connection.

4. The bioreactor cleaning system according to claim 3, wherein the suction unit and/or the supply unit are operable to pump liquid out of the acid tank and/or bioreactor to the first and/or second pH sensor and back into the acid tank and/or bioreactor.

5. The bioreactor cleaning system according to claim 3, wherein the electronic control unit is adapted to neutralize the aqueous acid solution present in the acid tank, while the suction unit and/or the supply unit pump the liquid out of the acid tank to the first or second pH sensor and back into the acid tank, to cause the base doser to dispense base into the mixer until a neutral target pH is reached in the acid tank.

6. The bioreactor cleaning system according to claim 1, wherein the acid doser comprises an acid ejector which can be connected to the freshwater connection on the input side of the acid doser.

7. The bioreactor cleaning system according to claim 1, wherein the base doser comprises a base ejector which can be connected to the freshwater connection on the input side of the base doser.

8. The bioreactor cleaning system according to claim 1, wherein the mixer comprises a throttle for throttling the freshwater supplied to the mixer.

9. The bioreactor cleaning system according to claim 1, further including:

a first flow meter for measuring the freshwater supplied to the mixer and/or the acid doser and/or the base doser.

10. The bioreactor cleaning system according to claim 9, further including:

a second flow meter for measuring the acid supplied to the acid doser.

11. The bioreactor cleaning system according to claim 1, wherein the suction unit and/or the supply unit are operable to pump liquid out of the acid tank and/or bioreactor to the mixer and back into the acid tank and/or bioreactor.

12. The bioreactor cleaning system according to claim 1, wherein the electronic control unit is adapted to:

determine an acid quality value indicating a quality of aqueous acid solution present in the acid tank;

compare the determined acid quality value to a predetermined acid comparison value; and depending on the comparison:

initiate neutralization of the aqueous acid solution in the acid tank.

13. The bioreactor cleaning system according to claim 12, wherein the electronic control unit is adapted to:

determine a first pH value of aqueous acid solution present in the acid tank;

compare the determined first pH value with a predetermined pH threshold value; and in the event that the determined first pH value exceeds the pH threshold value:

initiate neutralization of the aqueous acid solution in the acid tank.

14. The bioreactor cleaning system according to claim 13, wherein the electronic control unit is adapted to determine and load the acid comparison value and/or predetermined pH threshold value (SpH) from a database.

15. A method for operating a bioreactor cleaning system according to claim 1, comprising the steps:

determining an acid quality value indicating a quality of an aqueous acid solution present in an acid tank of the bioreactor cleaning system;

comparing the determined acid quality value to a predetermined acid comparison value; and depending on the comparison:

initiate neutralization of the aqueous acid solution in the acid tank.

16. The method of claim 15, wherein the acid quality value is a first pH-value, and wherein the method comprises the steps of:

determining a pH-value of aqueous acid solution present in the acid tank;

comparing the determined first pH-value with a predetermined pH threshold value; and in the event that the determined first pH-value exceeds the pH threshold value:

initiate neutralization of the aqueous acid solution in the acid tank.

17. The method according to claim 15, including:

determining and loading the acid comparison value and/or the predetermined pH threshold from a database.

18. The method according to claim 15, including:

pumping liquid out of the acid tank to a mixer of the bioreactor cleaning system and back into the acid tank.

19. The method of claim 15, including:

mixing in the mixer acid and/or base and/or freshwater.

20. The method according to claim 15, including:

determining a first pH-value downstream of the mixer.

21. The method according to any one of claim 20, including:

determining a second pH-value upstream of the mixer.

22. The method according to claim 21, including:

depending on the first and/or second pH-value, mixing in the mixer acid and/or base to achieve a neutral target pH in the acid tank.

23. The method of claim 22, wherein the neutral target pH is in a range of 6.5 to 10.

24. The method according to claim 23, including the step of:

when the neutral target pH is reached: pumping the liquid from the acid tank into a collection tank of the bioreactor cleaning system and/or a disposal drain.

25. The method according to claim 15, including:

dependent on the comparison: supplying liquid from the acid tank to the bioreactor for cleaning the bioreactor; and extracting liquid from the bioreactor and supplying the extracted liquid to the acid tank.

26. The method of claim 25, including:

introducing air in the form of bubbles into the liquid when supplying the liquid to the bioreactor.

* * * * *